(12) United States Patent
DiCesare et al.

(10) Patent No.: US 6,406,671 B1
(45) Date of Patent: Jun. 18, 2002

(54) DEVICE AND METHOD FOR SEPARATING COMPONENTS OF A FLUID SAMPLE

(75) Inventors: Paul C. DiCesare, Norwalk, CT (US); Richmond Cohen, Wanaque, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/454,268

(22) Filed: Dec. 3, 1999

Related U.S. Application Data

(60) Provisional application No. 60/110,937, filed on Dec. 5, 1998.

(51) Int. Cl.[7] .............................. B01L 11/00; B01L 3/00; G01N 1/18; B01D 12/00; B01D 17/00; B01D 43/00; B01D 21/26; B01D 33/15

(52) U.S. Cl. ..................... 422/101; 422/99; 422/102; 436/177; 436/178; 210/516; 210/518; 210/515; 210/512.1

(58) Field of Search ................... 422/99, 101, 102; 436/177, 178; 210/511, 512.1, 516, 533, 538, 518, 515

(56) References Cited

U.S. PATENT DOCUMENTS

| | | | | |
|---|---|---|---|---|
| 3,832,141 A | * | 8/1974 | Haldopoulos | 23/259 |
| 3,849,072 A | | 11/1974 | Ayers | |
| 4,055,501 A | * | 10/1977 | Cornell | 210/516 |
| 4,083,788 A | | 4/1978 | Ferrara | |
| 4,088,582 A | | 5/1978 | Murty et al. | |
| 4,131,549 A | | 12/1978 | Ferrara | |
| 4,152,270 A | | 5/1979 | Cornell | |
| 4,154,690 A | | 5/1979 | Ballies | |
| 4,257,886 A | | 3/1981 | Kessler | |
| 4,294,707 A | * | 10/1981 | Ikeda et al. | 210/782 |
| 4,295,974 A | * | 10/1981 | Cornell | 210/789 |
| 4,308,232 A | * | 12/1981 | Crouther et al. | 422/102 |
| 4,315,892 A | * | 2/1982 | Stone et al. | 422/101 |
| 4,364,832 A | | 12/1982 | Ballies | |
| 4,443,345 A | * | 4/1984 | Wells | 210/782 |
| 4,770,779 A | * | 9/1988 | Ichikawa et al. | 210/516 |
| 4,818,386 A | | 4/1989 | Burns | |
| 4,867,887 A | * | 9/1989 | Smith | 210/782 |
| 4,877,520 A | | 10/1989 | Burns | |
| 4,917,801 A | * | 4/1990 | Luderer et al. | 210/516 |
| 5,269,927 A | | 12/1993 | Fiehler | |
| 5,454,958 A | * | 10/1995 | Feihler | 210/782 |
| 5,455,009 A | | 10/1995 | Vogler et al. | |
| 5,575,778 A | | 11/1996 | Hardt et al. | |
| 5,632,905 A | | 5/1997 | Haynes | |
| 5,707,876 A | * | 1/1998 | Levine | 436/177 |
| 5,736,033 A | * | 4/1998 | Coleman et al. | 210/122 |
| 5,860,937 A | * | 1/1999 | Cohen | 600/576 |

FOREIGN PATENT DOCUMENTS

| | | |
|---|---|---|
| EP | 0 017 127 | 3/1980 |
| EP | 0 627 261 A2 | 6/1994 |
| EP | 0 638 804 A1 | 8/1994 |
| EP | 0 638 804 | 2/1995 |
| JP | 6-222055 | 8/1994 |

* cited by examiner

Primary Examiner—Jill Warden
Assistant Examiner—B. R Gordon
(74) Attorney, Agent, or Firm—Nanette S. Thomas

(57) ABSTRACT

A device and method is provided for separating heavier and lighter fractions of a fluid sample. The device includes a plurality of constituents comprising a container and a composite element in the container. The composite element is a separator comprising at least two components and more particularly an elastic portion and a plug member. A fluid sample is delivered to the container and the device is subjected to centrifugation whereby the centrifugal load causes the elastic portion of the separator to deform so that the separator migrates into the fluid sample and stabilizes between the heavier and lighter fractions of the fluid sample. The elastic portion of the separator will resiliently return to its initial configuration upon termination of the centrifugal load such that the elastic portion sealingly engages the container and separates the heavier and lighter fractions of the fluid sample.

4 Claims, 6 Drawing Sheets

DEVICE AND METHOD FOR SEPARATING COMPONENTS OF A FLUID SAMPLE

This application claims the benefit of U.S. Provisional Application(s) No(s).: APPLICATION NO(S).: 60/110,937 FILING DATE Dec. 5, 1998.

BACKGROUND OF THE INVENTION

1. Field of the Invention

This invention relates to a device and method for separating heavier and lighter fractions of a fluid sample. More particularly, this invention relates to a device and method for collecting and transporting fluid samples whereby the device and fluid sample are subjected to centrifugation to cause separation of the heavier fraction from the lighter fraction of the fluid sample.

2. Description of Related Art

Diagnostic tests may require separation of a patient's whole blood sample into components, such as serum or plasma, the lighter phase component, and red blood cells, the heavier phase component. Samples of whole blood are typically collected by venipuncture through a cannula or needle attached to a syringe or an evacuated collection tube. Separation of the blood into serum or plasma and red blood cells is then accomplished by rotation of the syringe or tube in a centrifuge. Such arrangements use a barrier for moving into an area adjacent the two phases of the sample being separated to maintain the components separated for subsequent examination of the individual components.

A variety of devices have been used in collection devices to divide the area between the heavier and lighter phases of a fluid sample.

The most widely used device includes thixotropic gel materials such as polyester gels in a tube. The present polyester gel serum separation tubes require special manufacturing equipment to prepare the gel and to fill the tubes. Moreover, the shelf-life of the product is limited in that over time globules may be released from the gel mass. These globules have a specific gravity that is less than the separated serum and may float in the serum and may clog the measuring instruments, such as the instrument probes used during the clinical examination of the sample collected in the tube. Such clogging can lead to considerable downtime for the instrument to remove the clog.

No commercially available gel is completely chemically inert to all analytes. If certain drugs are present in the blood sample when it is taken, there can be an adverse chemical interaction with the gel interface.

Therefore, a need exists for a separator device that (i) is easily used to separate a blood sample; (ii) is independent of temperature during storage and shipping; (iii) is stable to radiation sterilization; (iv) employs the benefits of a thixotropic gel barrier yet avoids the many disadvantages of placing a gel in contact with the separated blood components; (v) minimizes cross contamination of the heavier and lighter phases of the sample during centrifugation; (vi) minimizes adhesion of the lower and higher density materials against the separator device; (vii) can be used with standard sampling equipment; (viii) is able to move into position to form a barrier in less time than conventional methods and devices; and (ix) is able to provide a clearer specimen with less cell contamination than conventional methods and devices.

SUMMARY OF THE INVENTION

The present invention is a method and assembly for separating a fluid sample into a higher specific gravity phase and a lower specific gravity phase. Desirably, the assembly of the present invention comprises a plurality of constituents. Preferably, the assembly comprises a container and a composite element.

Most preferably, the container is a tube and the composite element is a separator arranged to move in the tube under the action of centrifugal force in order to separate the portions of a fluid sample. Preferably, the separator is a radically deformable seal plug.

Most preferably, the separator is used within a container such as a tube. The tube comprises an open end, a closed end and a sidewall extending between the open end and closed end. The sidewall comprises an outer surface and an inner surface. The tube further comprises a closure disposed to fit in the open end of the tube with a resealable septum. Preferably, the separator element is releaseably positioned at the open end of the tube with the bottom area of the closure.

Most preferably, the separator consists of two components. Preferably, the composite element comprises an overall specific gravity at a target specific gravity of $\sigma_t$. The target specific gravity is that required to separate a fluid sample into at least two phases. Preferably, the separator comprises at least two or more regions of differing specific gravities. Preferably, at least one of the regions is higher than the target specific gravity and at least one of the regions is lower than the target specific gravity.

Desirably, the separator comprises a low density plastic body and a high density elastomeric seal diaphragm. The separator as a whole is sized to fit releasably within the tube with an interference fit against the inner surface of the sidewall of the tube.

Preferably, the plastic body has a hollow core or a central passage and a hollow chamber surrounding the hollow core. The plastic body has a specific gravity of about 1.1 to about 7.9.

Desirably, the plastic body is a substantially rigid moldable thermoplastic material such as polystyrene, polyethylene, polypropylene, and mixtures thereof that is inert to the fluid sample of interest.

Desirably, the elastomeric seal diaphragm comprises a fill septum to facilitate needle penetration during the blood fill cycle and an annular skirt that is able to deform during the centrifugation process and reduce the overall diameter of the separator.

Desirably, the plastic body is nested within the elastomeric seal diaphragm, whereby the channel of the plastic body is in direct communication with the fill septum of the elastomeric seal diaphragm.

Desirably, the elastomeric seal diaphragm may be comprised of any natural or synthetic elastomer or mixture thereof, that is inert to the fluid sample of interest. Preferably, the elastomeric seal diaphragm is made from an elastomer having a 50% tensile modulus from about 0.1 MPa to about 1.4 MPa.

Preferably, the separator has a density of about 1.028 to about 1.09 g/cc so that the separator will come to rest after centrifugal force, at substantially at the border between the heavier and lighter phases of the fluid sample under consideration, and most preferably between the heavier and lighter phases of a blood sample. Preferably, the separator will function under load created by an applied acceleration of about 300 g to about 3000 g.

Preferably, the separator is initially secured to the bottom area of the closure. Desirably, the bottom area of the closure includes an integrally molded gripping means for releasably holding the elastomeric seal diaphragm of the separator with the closure until the assembly is subjected to centrifugation at which time the separator is released from the gripping means of the closure. The separator is further fitted with the tube whereby the annular skirt of the elastomeric seal diaphragm, which provides the largest diameter of the separator in its undeformed state, has an interference fit with the inner surface of the sidewall of the tube.

In use, a fluid sample enters the assembly by needle. The needle penetrates the closure and the elastomeric seal diaphragm of the separator. The sample enters the assembly through the needle and through the channel of the plastic body and into the body of the tube. The needle is withdrawn from the assembly and the septum of the closure and the elastomeric seal diaphragm reseal.

The assembly is then subjected to centrifugation. Under centrifugation, the separator is released from the closure. The separator migrates axially down the tube towards the closed end. The migration is facilitated by the density of the plastic body versus the density of the elastomeric seal diaphragm of the separator. The annular skirt of the elastomeric seal diaphragm temporarily deforms under centrifugation, whereby the diameter is reduced eliminating its interference fit with the inner wall surface of the tube. Therefore, a path is developed between the inner wall of the tube and the separator that permits the flow of the low density component past the separator as it migrates down the tube. Migration of the separator terminates when it reaches the position between the lower density liquid component and higher density cellular/solid components, equal to its overall density. Upon terminating centrifugation, the annular skirt of the elastomeric seal diaphragm returns to its undeformed shape, sealing against the inner wall of the tube, thereby creating a barrier between the higher and lower density components of the fluid.

The separator's position at the top of the tube in conjunction with the closure and the elastomeric seal diaphragm's penetrable area into the passage throughway of the separator, provides easy direct loading of the fluid sample into the tube without any obstructions. Thus, the fluid sample is easily delivered into the tube without exposing the uncentrifuged fluid sample to the outer surface area of the separator.

However, it is within the purview of the invention that the separator may be placed at the bottom of the tube as well.

Thus, when the container is subjected to centrifugation, the separator moves away from the grip of the closure and towards a position between the lower and higher specific gravity phases of the fluid sample.

When the fluid sample is blood, the higher specific gravity portion that contains the cellular components is between the separator and the bottom of the container after centrifugation. The lower specific gravity portion that contains the cell free serum fraction or plasma is between the top surface of the separator and the top of the container after centrifugation.

Therefore, at the final position of the separator after centrifugation, the separator is able to substantially eliminate the presence of red blood cells in the lower specific gravity portion and the lower specific gravity portion is substantially free of cellular contamination.

The assembly of the present invention is advantageous over existing separation products that use gel. In particular the assembly of the present invention will not interfere with analytes as compared to gels that may interfere with certain analytes. Another attribute of the present invention is that the assembly of the present invention will not interfere with therapeutic drug monitoring analytes.

Most notably, the time to separate a fluid sample into separate densities is achieved in substantially less time with the assembly of the present invention as compared to assemblies that use gel.

Another notable advantage of the present invention is that fluid specimens are not subjected to low density gel residuals that are at times available in products that use gel.

A further attribute of the present invention is that there is no interference with instrument probes.

Another attribute of the present invention is that samples for blood banking tests are more acceptable than when a gel separator is used.

Another attribute of the present invention is that only the substantially cell-free serum fraction of a blood sample is exposed to the top surface of the separator, thus providing practitioners with a clean sample.

Additionally, the assembly of the present invention does not require any additional steps or treatment by a medical practitioner, whereby a blood or fluid sample is drawn in the standard fashion, using standard sampling equipment.

DETAILED DESCRIPTION

Figure 1:
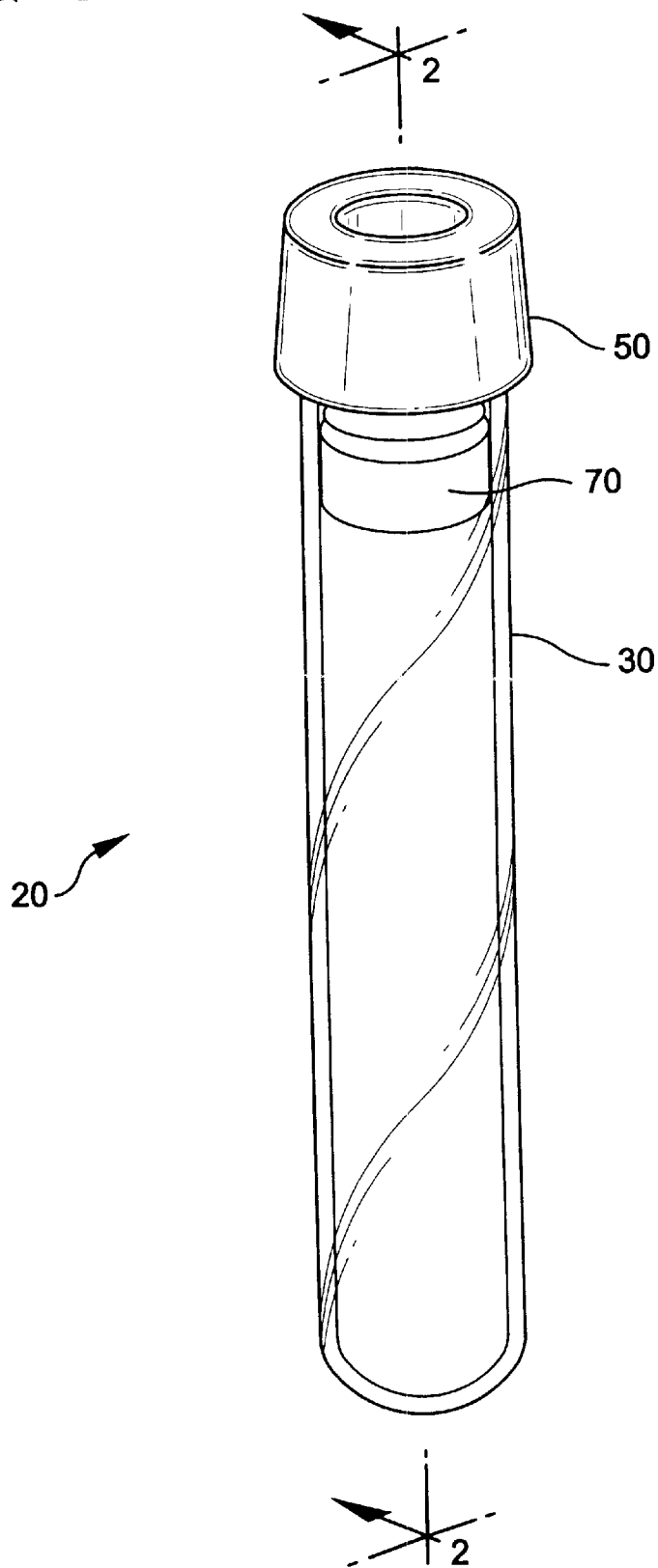
FIG. 1 is a perspective view of the assembly of the present invention.

The present invention may be embodied in other specific forms and is not limited to any specific embodiments described in detail, which are merely exemplary. Various other modifications will be apparent to and readily made by those skilled in the art without departing from the scope and spirit of the invention. The scope of the invention will be measured by the appended claims and their equivalents.

The preferred apparatus of the present invention is illustrated in FIGS. 1 to 5, wherein assembly 20 comprises a tube 30, a closure 50 and a separator 70.

Tube 30 has an open end 32 that includes a top edge 33, a closed end 34 and a sidewall 36 extending between the open end and the closed end. Sidewall 36 has an outer surface 38 and an inner surface 40. Tube 30 defines a receptacle with a central axis "A".

Tube 30 is preferably made from a substantially transparent and rigid material. Suitable materials for the tube include glass, polystyrene, polyethyleneterephthalate, polycarbonate and the like.

Closure 50 is disposed to fit over open end 32 of tube 30. Closure 50 comprises an annular upper portion 52 which extends over top edge 33 of sidewall 36 and a lower annular portion or skirt 54 of lesser diameter than the annular upper portion 52 which extends into and forms an interference fit with inner surface 40 of sidewall 36 for maintaining stopper 50 in place in open end 32.

Annular upper portion 52 includes a top surface area 56, sidewall 58 that converges from surface area 56 towards upper well area 60. Well area 60 is most preferably a thin diaphragm or a self sealing septum for directing and receiving the point of a needle to be inserted into and through the stopper. The self sealing septum material allows penetration by a piercing element such as a needle and then reseals when the piercing element is withdrawn.

An annular ledge or abutment 57 separates annular upper portion 52 and lower annular portion 54. Located on bottom surface 68 of lower annular portion 54 are gripping means 69 that are used to initially align and hold the separator in the assembly.

Preferably, the closure may be made of natural rubber elastomer, synthetic thermoplastic and thermoset elastomeric materials. Preferably, the closure is made of a resilient elastomeric material whereby the septum is self-sealing.

Figure 6:
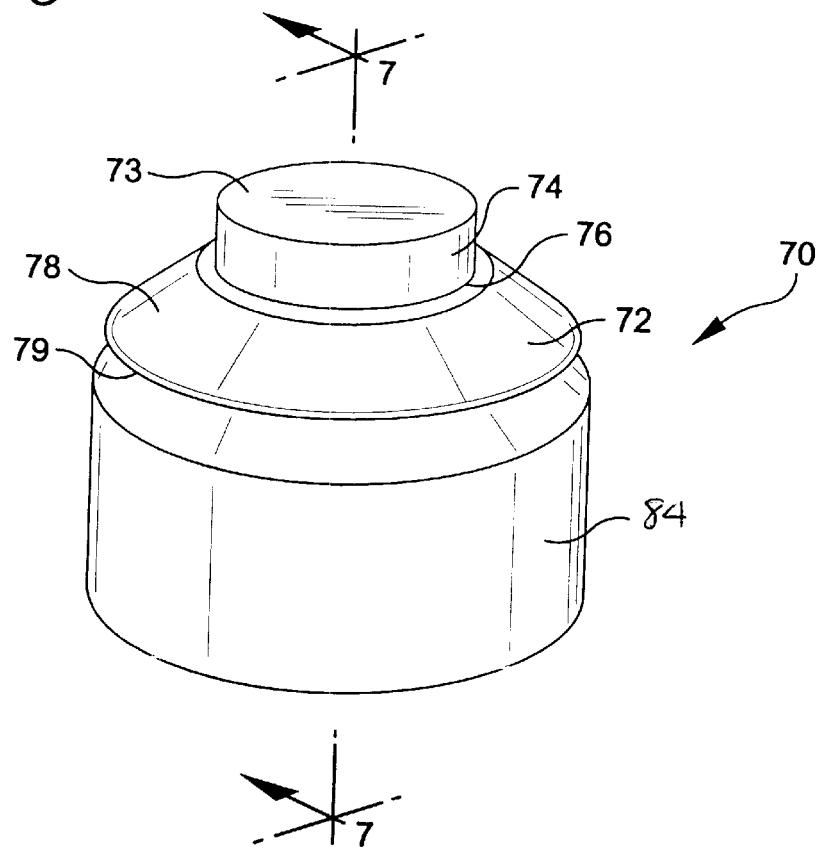
FIG. 6 is a perspective view of the separator of the present invention.
Figure 7:
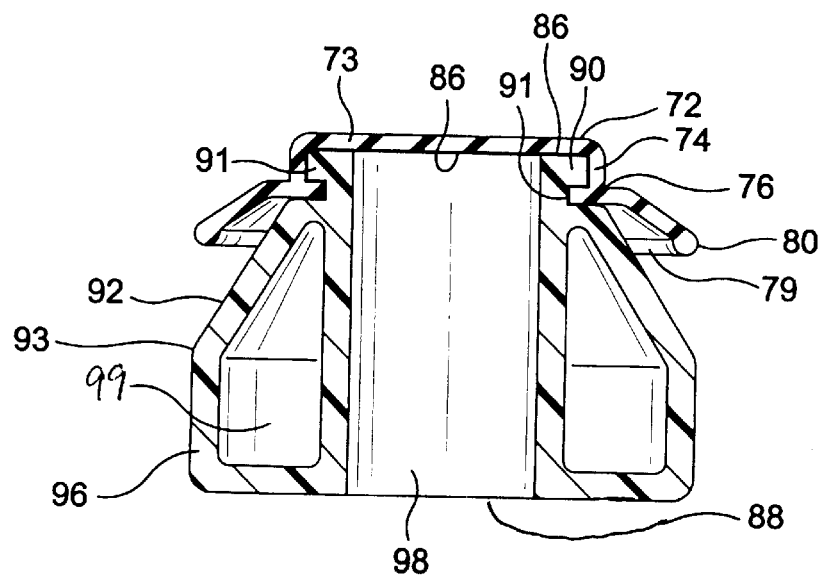
FIG. 7 is a longitudinal sectional view of the separator of FIG. 6 taken along line 7—7 thereof.

As shown in FIGS. 6 and 7, separator 70 is a dual separator assembly including a molded seal body 84 and an elastomeric hat shaped flexible seal diaphragm 72. Flexible seal diaphragm 72 includes a top surface 73, an annular skirt 74 extending downwardly from the top surface to a junction 76 and a flanged annular skirt 78 extending outwardly and downwardly from the junction to a stop surface 79 with a rounded end 80. Top surface 73 is most preferably a self sealing septum.

Seal body 84 includes a top surface 86, a bottom surface 88, an annular upper portion 90 extending from the top surface to an indented junction 91, a flanged outer sidewall 92 extending downwardly and outwardly and tapers towards a junction 93, and a second outer sidewall 96 extending from junction 93 downwardly to bottom surface 88. Inside of seal body 84 is a passageway 98 and a cavity 99. Passageway 98 extends from top surface 86 to bottom surface 88. Passageway 98 mates with top surface 73 of annular skirt 74 of flexible seal diaphragm 72 whereby when a piercing element goes through top surface 73 it will extend directly into passageway 98 without any interference.

Figure 2:
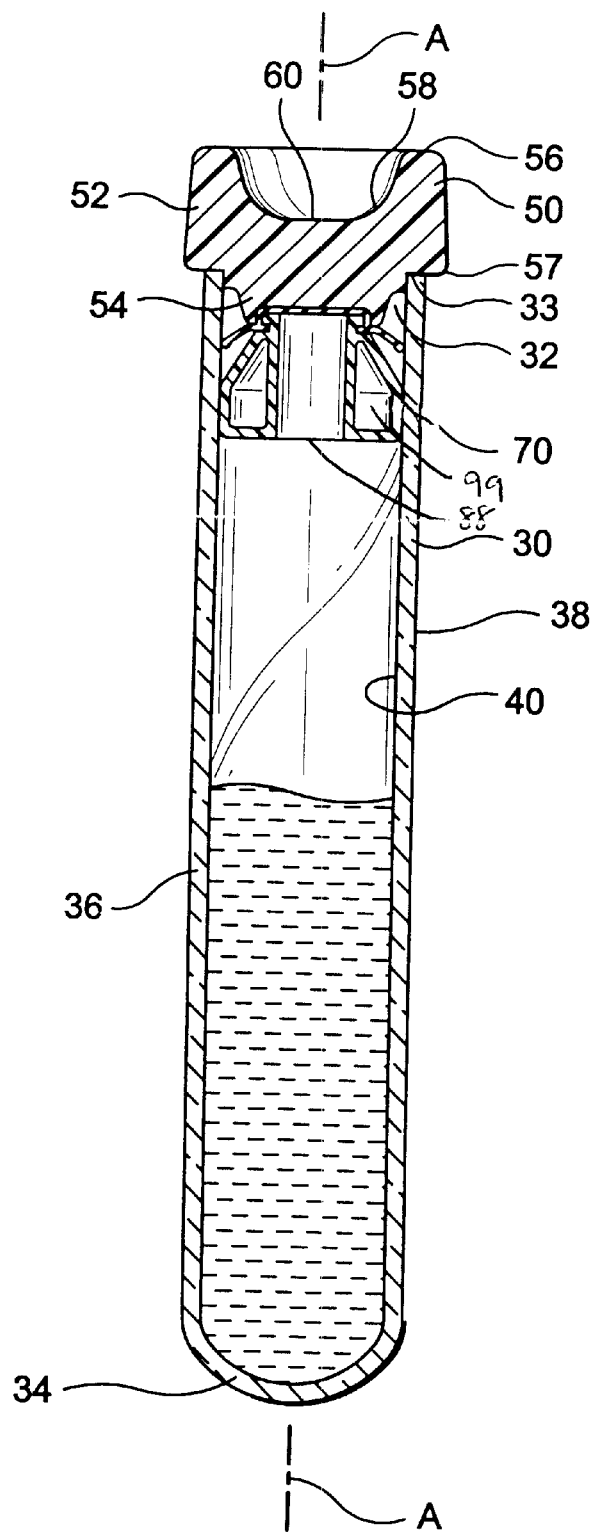
FIG. 2 is a longitudinal sectional view of the assembly of FIG. 1 taken along line 2—2 thereof.

As shown in FIG. 7, annular upper portion 90 of seal body 84 is nested in annular skirt 74 of flexible seal diaphragm 72. Friction fit, an adhesive or the like may be used to maintain the nesting of the two components. The separator is then held at the top end of the tube by gripping means 69 of the closure. As shown in FIG. 2, rounded end 80 of flexible seal diaphragm 72 and the inner wall of the tube form an interference fit. The seal body does not interfere with the inner wall of the tube as shown in FIG. 2, because the diameter of flanged annular skirt 78 of flexible seal diaphragm 72 is larger than the diameter of seal body 84.

Figure 3:
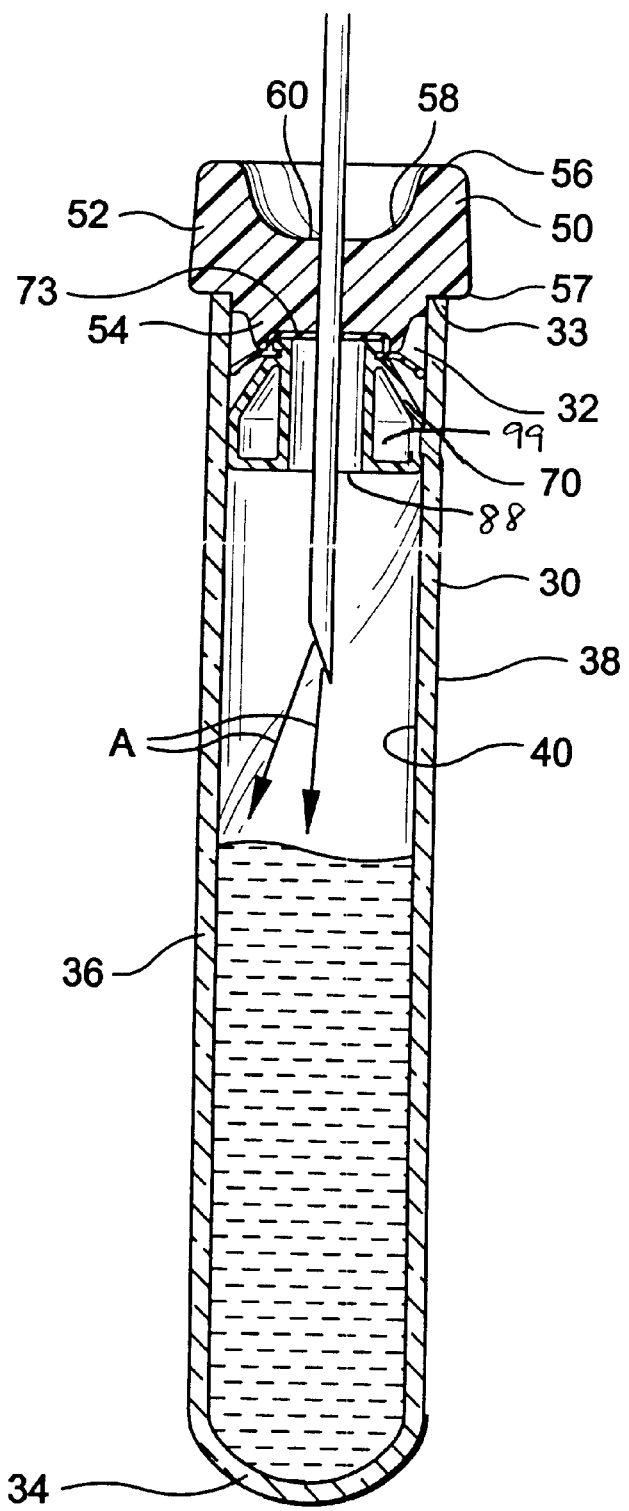
FIG. 3 is a longitudinal sectional view of the assembly of FIG. 1 taken along line 2—2 thereof illustrating fluid delivery into the assembly by a needle.

As shown in FIG. 3, a fluid sample A is delivered to the tube by a needle that penetrates closure 50 in upper well area 60, then top surface 73 of flexible seal diaphragm 72 and bottom surface 88, which is preferably a resealable septum material. For purposes of illustration only, the fluid sample is blood. The fluid sample is delivered into the axial passageway of the separator so that the fluid sample is introduced between closed end 34 of the tube and the separator whereby the outer surface of all components of the separator are substantially free of any contact with the fluid sample.

Figure 4:
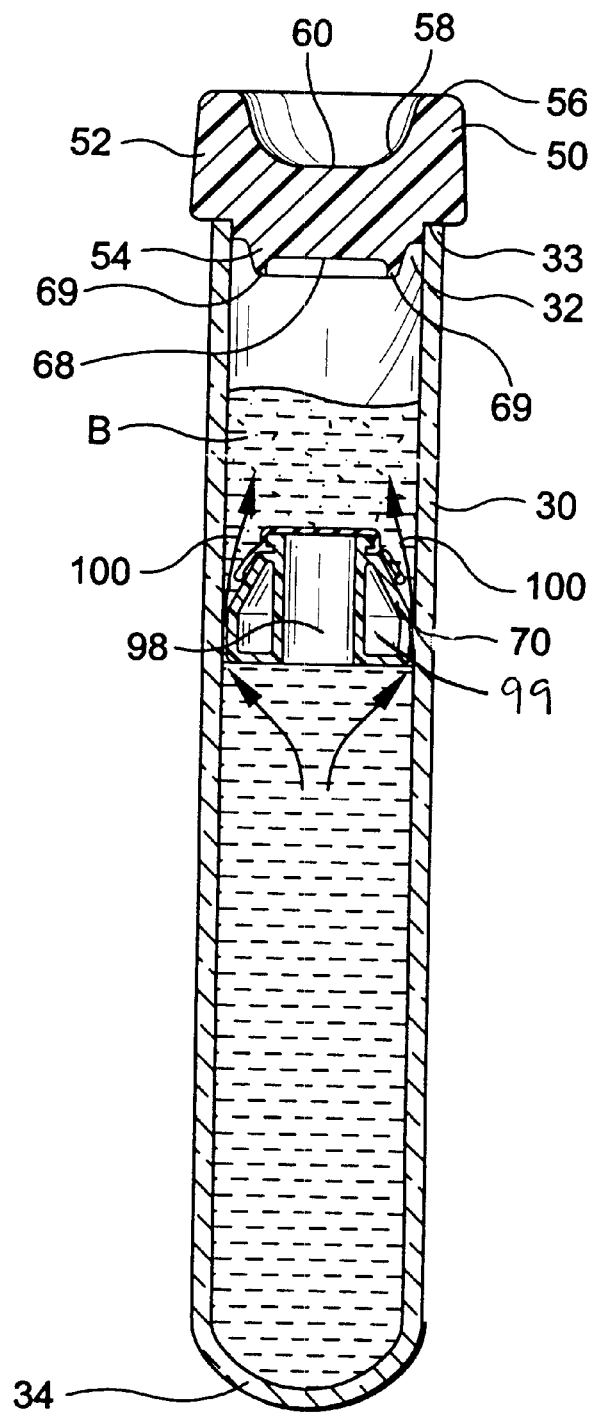
FIG. 4 illustrates the assembly under centrifugation and the release of the separator from the gripping means of the closure.

As shown in FIG. 4 when assembly 20 is subjected to centrifugation or axial centrifugation force, separator 70 releases from gripping means 69 of closure 50 and descends towards closed end 34 of tube 30. As the separator descends, a lower specific gravity fraction B of fluid sample A moves upwardly past the separator.

As shown in FIG. 4 as the separator descends, flanged annular skirt 78 of the elastomeric seal deforms, reducing its diameter and eliminating its interference with the inner wall of the tube. This opens up a path 100 between the tube and the separator, permitting the flow of the fluid past the separator as the separator migrates down the tube. The residual low density component inside passageway 98 of the separator will migrate downwardly and upwardly past the separator.

Figure 5:
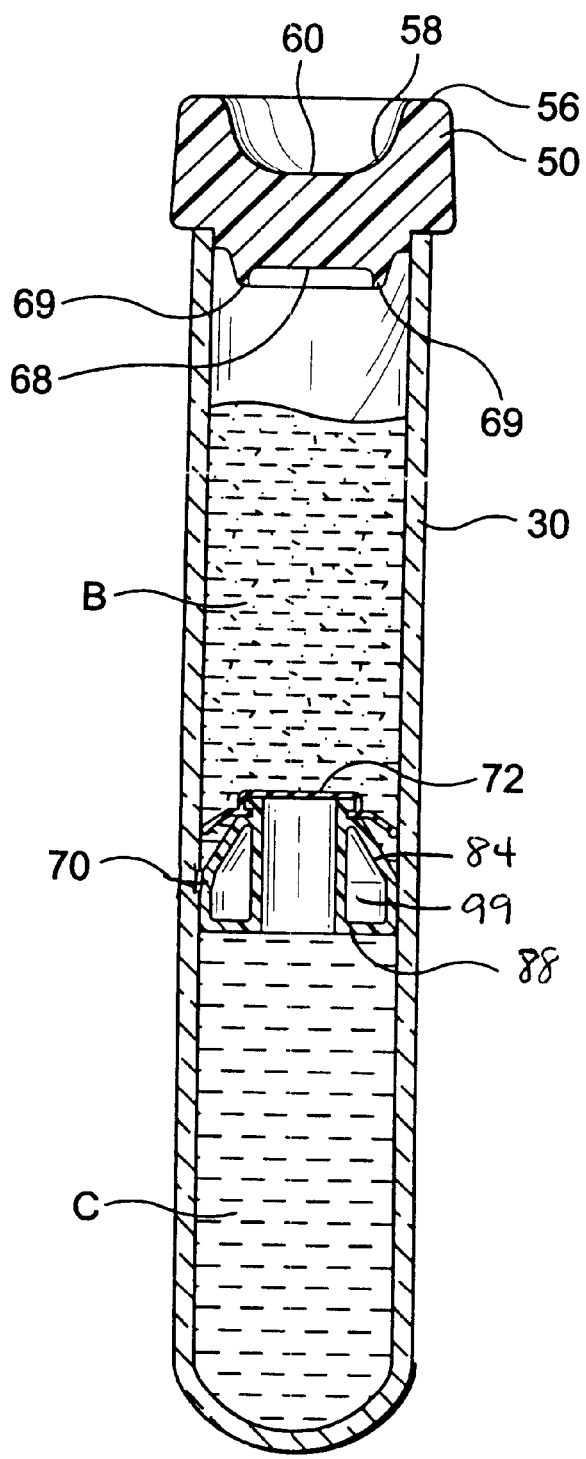
FIG. 5 illustrates the assembly after certrifugation and the separation of the liquid sample into higher and lower specific gravities.

As illustrated in FIG. 5, after centrifugation is complete, centrifugation is terminated, the elastomeric seal diaphragm returns to its undeformed shape, sealing against the inner wall of the tube, whereby separator 70 serves as a divider between lower specific gravity portion B and higher specific gravity portion C of the fluid sample.

Tube 30 is compatible with most of the numerous additives used in sample collection tubes such as citrates, silicates, EDTA and the like that are used to condition the sample either to facilitate or retard clotting, or to preserve the sample for a particular analysis. It is within the purview of this invention that one or more additives may be used in the present invention for particular applications.

What is claimed is:

1. An assembly for separating a fluid sample into a higher specific gravity phase and a lower specific gravity phase comprising:

a tube comprising an open end, a closed end, an inner diameter, an outer diameter and a sidewall extending between said open end and said closed end, whereby said sidewall comprises an outer surface and an inner surface;

a closure disposed in said open end of said tube comprising a resealable septum;

a separator element comprising a plastic body and an elastomeric seal diaphragm in said tube;

said plastic body comprising a hollow core and a hollow chamber surrounding said hollow core;

said elastomeric seal diaphragm comprising a fill septum and an annular skirt; and said plastic body is nested with said elastomeric seal diaphragm whereby said hollow core of said plastic body is in direct communication with said fill septum of said elastomeric seal diaphragm.

2. An assembly for separating a fluid sample into a higher specific gravity phase and a lower specific gravity phase comprising:

a tube comprising an open end, a closed end, an inner diameter, an outer diameter and a sidewall extending between said open end and said closed end;

said sidewall comprising an outer surface and an inner surface;

a closure disposed in said open end of said tube;

a separator element in said tube movable axially in said tube under the action of centrifugal force;

said separator element providing selectively an annular seal and an open passage there around in response to an applied force to said tube;

said separator element comprising a plastic body and an elastomeric seal diaphragm;

said elastomeric seal diaphragm comprising a fill septum and an annular skirt that provides an interference fit with said inner surface of said sidewall of saidtube;

said plastic body comprising a hollow core chamber surrounding said hollow core so as to direct said fluid sample into said assembly;

said plastic body is nested with said elastomeric seal diaphragm whereby said hollow core of said plastic body is in direct communication with said fill septum of said elastomeric seal diaphragm;

wherein said separator is located at said open end of said tube by an interference fit between said elastomeric seal diaphragm and said inner diameter of said tube.

3. A method for separating a fluid sample into a higher specific gravity phase and a lower specific gravity phase, comprising the steps of:

(a) providing a tube comprising an open end, a closed end, an inner diameter, an outer diameter and a sidewall extending between said open end and said closed end and comprising an outer surface and an inner surface;

(b) providing a closure disposed in said open end of said tube comprising a resealable septum;

(c) providing a separator element comprising an elastomeric seal diaphragm and a plastic body whereby said elastomeric seal diaphragm comprises a fill septum and an annular skirt that provides for selectively providing an interference fit and an open passage with said inner surface of said sidewall of said tube in response to equal or different pressures above and below said separator, and a hollow core extending through said plastic body; said plastic body is nested with said elastomeric seal diaphragm whereby said hollow core of said plastic body is in direct communication with said fill septum of said elastomeric seal diaphragm;

(d) providing said separator element in said tube whereby said elastomeric seal diaphragm comprises an interference fit with said inner wall;

(e) providing a needle that penetrates said closure and said septum of said elastomeric seal diaphragm;

(f) delivering a fluid sample to said tube whereby said sample enters through said needle and through said septum and said hollow core of said plastic body and then into said boy of said tube;

(g) removing said needle from said assembly whereby said septum of said closure and said elastomeric seal diaphragm reseals;

(h) subjecting said tube with said separator element to centrifugation whereby said elastomeric seal diaphragm separates from said inner wall of said tube and said separator migrates axially in said tube whereby the low density component of the sample passes above the separator; and (i) terminating said centrifugation whereby said elastomeric seal diaphragm expands to its underformed shape, sealing against said inner wall of said tube, thereby creating a barrier between said higher and lower density components of said fluid sample.

4. A separator for use with a specimen collection tube for separating of a fluid specimen into phases having different densities, said separator comprising a molded seal body and an elastomeric flexible seal diaphragm; said elastomeric flexible seal diaphragm comprising a top surface, a junction, a stop surface, an annular skirt extending downwardly from said top surface to said junction; and a flanged annular skirt extending outwardly and downwardly from said junction; and a flanged annular skirt extending outwardly and downwardly from said junction to said stop surface;

said seal body comprising a top surface, an indented junction, a bottom surface, an annular upper portion extending from said top surface to said indented junction, a flanged outer sidewall extending downwardly, outwardly and tapering towards said junction, a second outer sidewall extending from said junction downwardly to said bottom surface and a passageway extending from said top surface to said bottom surface through said seal body; whereby said annular upper portion of said seal body is nested with said annular skirt of said flexible seal diaphragm and said passageway of said seal body mates with said top surface of said flexible seal diaphragm.

* * * * *